United States Patent [19]

Brace

[11] Patent Number: 5,614,718
[45] Date of Patent: Mar. 25, 1997

[54] APPARATUS AND METHOD FOR NONINVASIVE ASSESSMENT OF PRESSURIZED CONTAINER PROPERTIES

[75] Inventor: John G. Brace, Saline, Mich.

[73] Assignee: Hoover Universal, Inc., Plymouth, Mich.

[21] Appl. No.: 538,722

[22] Filed: Oct. 3, 1995

[51] Int. Cl.$^6$ ........................................... G01T 3/00
[52] U.S. Cl. ........................... 250/339.13; 250/339.07; 250/339.09; 250/343
[58] Field of Search ........................... 250/338.1, 339.07, 250/339.13, 340, 343, 373, 339.09

[56] References Cited

U.S. PATENT DOCUMENTS 5,473,161 12/1995 Nix et al. .................................. 250/343

Primary Examiner—David P. Porta
Assistant Examiner—David Vernon Bruce
Attorney, Agent, or Firm—Harness, Dickey & Pierce, P.L.C.

[57] ABSTRACT

A method and apparatus for the rapid estimation of the gas concentration within the headspace of a production beverage container which contains a carbonated beverage, includes preparing a prediction model based on correlations between an infrared absorption spectrum obtained from an analysis container and corresponding measured values of gas concentrations and physical properties of the analysis container, the method, whereby the physical property or gas concentration within the headspace of production container do not need to be measured directly, but rather are estimated based on the prediction model with a measured infrared absorption spectrum as an input to the prediction model, thereby providing non-invasive monitoring of production containers, filled and pressurized.

12 Claims, 5 Drawing Sheets

APPARATUS AND METHOD FOR NONINVASIVE ASSESSMENT OF PRESSURIZED CONTAINER PROPERTIES

BACKGROUND OF THE INVENTION

The present invention relates generally to the field of test apparatus, and more particularly to apparatus for providing noninvasive assessment of properties of pressurized containers.

Articles formed of plastic materials are often used as containers for food, beverages, or the like, and such containers are generally designed to give certain performance properties. One function of packaging is to form a barrier against permeation of gasses to or from the food product. For example, reduction of the carbon dioxide permeation rate helps to maintain a high level of carbonation in carbonated beverages. Therefore, the choice of suitable plastic material is obviously important, as well as the distribution of material and the processing conditions, as is well known in the blow molding art.

A major difficulty with volume production of plastic containers is that periodic sampling of production containers is required to ensure that the container is performing to the desired specifications. In the prior art, the periodic sampling required actual, direct measurement of the physical property of interest. Some of the required measurements, however, are extremely painstaking and time consuming to perform. In the case of the carbonation retention, for example, the actual, direct measurement thereof requires a substantial amount of large test equipment and apparatus, including plumbing, precision gas detectors, etc. In addition, the decrease in carbonation level of a sealed container is so low that a test cycle usually lasts for several weeks, before an estimate of carbonation loss rate can be obtained for predicting the shelf life of a consumer product, such as carbonated beverages. Related to this are the physical and material properties of the container which effect and affect the carbonation retention capability of such containers.

Known prior methods require removing all or a portion of either the headspace gases, or the liquid, for analysis. Prior analysis techniques include (a) gas chromatography which involves separation and detection of gases; (b) conductometric titration which involves detection of dissolved ionic species, e.g. $HCO_3^-$; (c) simple headspace pressure determination of all gases, non selectively; (d) the use of a $CO_2$-permeable pH probe; and (e) the use of infrared absorption in an external cell. None of these prior art methods contemplate direct examination of an intact, capped, pressurized plastic container that has been filled with a product under pressure and then sealed, to determine the concentration of at least one gas in the headspace of such container.

Accordingly, a need exists for a faster, simpler method for providing nondestructive carbonation-retention monitoring and performance prediction in beverage containers. Moreover, it would be desirable to be able to quickly predict the processing effects on materials properties and to evaluate container-to-container variation.

SUMMARY OF THE INVENTION

The present invention provides a method and apparatus for measuring the concentration of at least one gas in the headspace of a plastic container that has been filled with a product and then sealed under pressure. The method of the invention comprises the steps of (a) preparing a prediction model which accepts as an input at least one spectral component value corresponding to absorption of electromagnetic radiation in at least one frequency band of the radiation, and which outputs an estimated measurement for the concentration of the at least one gas in the headspace of the container based on the input; (b) performing spectroscopic analysis of the container to obtain at least one spectral component value corresponding to the absorption of electromagnetic radiation in the at least one frequency band by the at least one gas; and (c) evaluating the prediction model with the at least one spectral component value as the input, wherein the output of the prediction model is thereby a measurement of the concentration of the at least one gas in the headspace of the container. The electromagnetic radiation preferably is in the infrared spectrum.

In accordance with the method of the invention the prediction model is prepared by (d) measuring at least one physical property of an analysis container to thereby obtain first measurement data representing a measured value for the at least one physical property; (e) filling the analysis container with the at least one gas under pressure; (f) measuring the pressure within the analysis container to obtain second measurement data representing the pressure within the analysis container; (g) performing spectroscopic analysis of the analysis container to obtain at least a first analysis spectral component value corresponding to the at least one physical property and at least a second analysis spectral component value corresponding to the absorption of electromagnetic radiation in the at least one frequency band by the at least one gas; (h) computing correlations between at least the first analysis spectral component values and the first measurement data and between at least the second analysis spectral component values and the second measurement data; and (i) performing multivariate regression analysis on the analysis spectral component values with respect to the measured value for pressure of at least the one gas and the measured value of the at least one physical property to produce the prediction model as an equation which maps spectral components as inputs to an estimated value for the pressure of the at least one gas and the at least one physical property as an output.

The invention further provides apparatus for measuring the concentration of at least one gas in the headspace of a container that has been filled with a product and then sealed under pressure. The apparatus comprises means for providing a prediction model which accepts as an input at least one spectral component value corresponding to absorption of electromagnetic radiation in at least one frequency band of the radiation, and which outputs an estimated measurement for the physical property based on the input; means for performing spectroscopic analysis of the container to obtain at least one spectral component value corresponding to the absorption of electromagnetic radiation in the at least one frequency band by the gas; and means for evaluating the prediction model with the at least one spectral component value as the input, wherein the output of prediction model is thereby a measurement of the concentration of at least the one gas in the headspace of the container. The means for providing the prediction model includes means for providing measurement data representing the pressure within an analysis container; means for performing spectroscopic analysis of an analysis container to obtain at least one spectral component value corresponding to the absorption of electromagnetic radiation in the at least one frequency band by the at least one gas; and processing means for computing correlations between the spectral component value and the measurement data and for performing multivariate regression analysis on the analysis spectral component values with respect to the measured value for the concentration of the at least one gas in the analysis container and to produce an equation which maps spectral components as inputs to an estimated value for the concentration of the at least one gas in the analysis container as an output.

The method and apparatus of the invention is particularly adapted for nondestructive monitoring of carbonation retention for beverage containers containing carbonated beverages, for providing direct prediction of carbonation loss rate. Because headspace composition $CO_2$ level is available noninvasively, filled and capped containers can be monitored in a direct relevant quality control operation.

DETAILED DESCRIPTION OF A PREFERRED EMBODIMENT

This invention relates to a method and apparatus for rapidly and noninvasively acquiring information relating to containers. The invention is particularly useful for monitoring beverage containers containing carbonated beverages to obtain information indicative of headspace gas concentrations and selected material properties of the containers. The information obtained permits prediction of carbonation loss rate for such containers and the determination of processing effects on the materials from which the container is produced.

Figure 1:
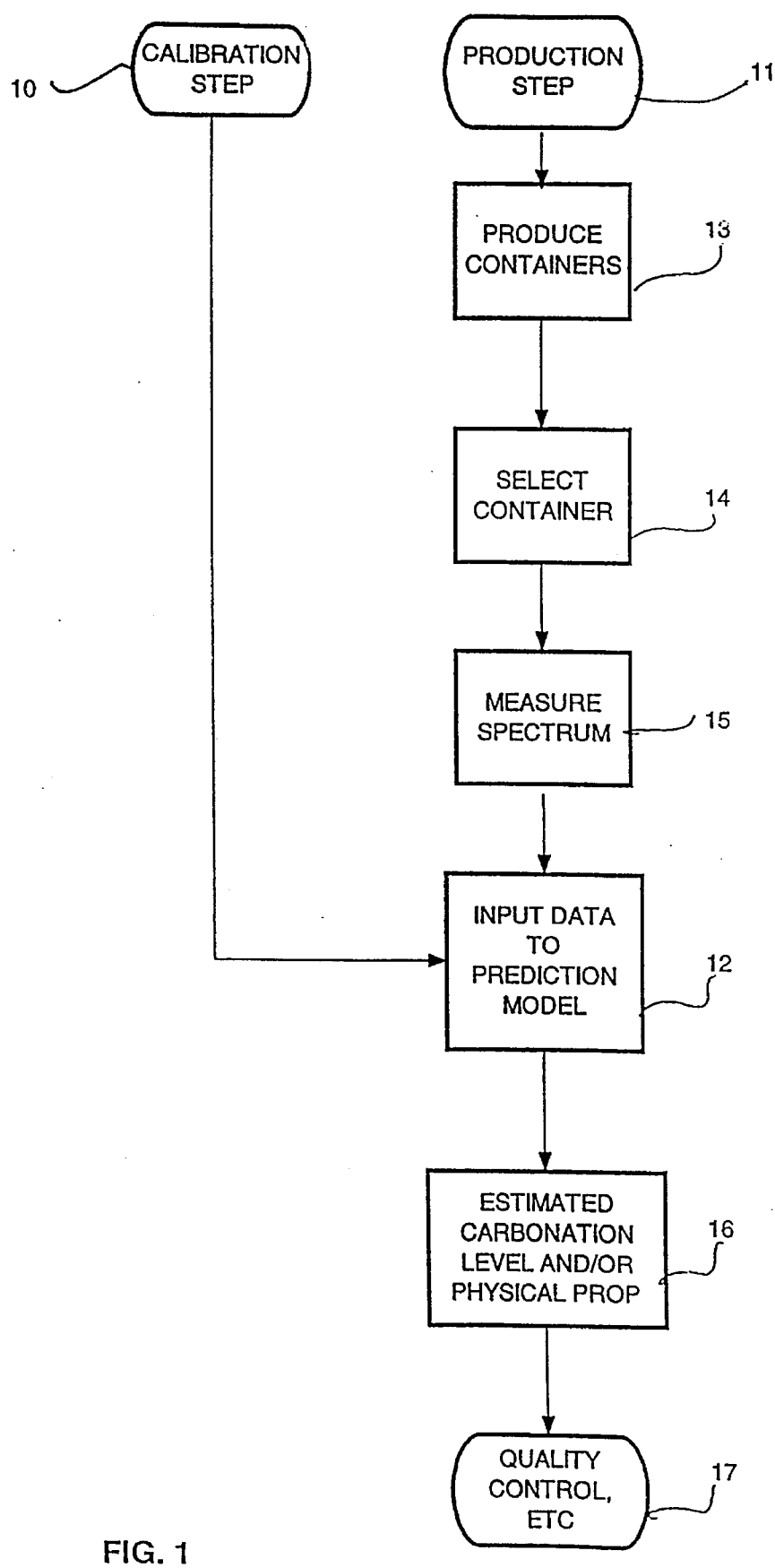
FIG. 1 is a process flow chart illustrating the method of the invention.

Referring to the drawings, FIG. 1 is a flow chart illustrating the process steps for the method of the present invention. The method includes a calibration step, which is indicated at block 10, and a production step initiated at block 11 and which includes the process steps 13–17. Briefly, in the calibration step 10, which includes steps 30–40 illustrated in detail in FIG. 4, a prediction model is prepared based on both a spectroscopic analysis of one or more analysis containers and on data obtained from measurement of one or more physical properties of the analysis container. The analysis containers are subjected to spectral analysis using near infrared (NIR) transmission through the analysis container to acquire information in the form of spectral signatures from one and preferably a plurality of analysis containers. The spectral signatures obtained are analyzed for qualitative features that allow accurate classification of container style and material and for intensity patterns that allow quantitative analysis of the containers, and which permit a prediction model to be created. In addition, the analysis container is physically measured to produce calibration data indicative of the physical construction of the container. The prediction model that is prepared in the calibration step 10 is then later used in the production step 11, as indicated by reference numeral 12, for monitoring production containers. In the exemplary embodiment, the prediction model is used in the production step to permit noninvasive monitoring of production containers for predicting carbonation retention and measuring physical characteristics of the production containers to provide information for use in estimating the performance of the containers and the shelf-life of a product, such as a carbonated beverage, stored in the containers.

In the process step, represented by blocks 13–17 in FIG. 1, a container to be analyzed is selected from a batch of production containers and is subjected to spectroscopic analysis. The method of the invention utilizes spectroscopic analysis so that the monitoring function can be performed relatively rapidly and is amenable to automated testing and without the necessity for performing an actual physical measurement of the containers. The spectrum obtained provides inputs to the prediction model, block 12, to enable evaluation of the selected container to provide information for use in process control, quality control, and the like. The information that is provided through the spectroscopic analysis is indicative of absorption bands in the near infrared and allows quantifying the concentration or pressure of specific gasses within the analysis container which, in the exemplary embodiment, includes measurement of the headspace gas concentrations to permit prediction of carbonation loss rate.

The invention is equally applicable to quantifying other major gaseous components in the headspace. However, the gases must be volatile and must absorb NIR radiation reasonably strongly because NIR analysis is not a trace analysis technique. Other volatile flavor components for carbonated beverages, such as higher alcohols, glycol aldehydes, ketones or esters, also are NIR-active and it may be possible to quantify such components using the method of this invention.

Another monitoring method which involves the use of a prediction model and spectroscopic analysis is disclosed in my U.S. Pat. No. 5,381,228 which was issued on Jan. 10, 1995, and which patent is incorporated herein by reference. This patent discloses a method and apparatus for monitoring physical properties, including oxygen permeation rate, of thin film coatings applied to articles, such as containers for consumable food products and the like.

Digressing, the basic requirements for successful container property estimations are that the properties be dependent on the molecular structure of the material of which the container is made; that changes in molecular structure associated with changes in the property be reflected in the infrared spectra; and that the properties be reasonably linearly related to spectral intensities. The frequencies, or spectral range, needed to meet these requirements depend to some extent on the polymer, laminate or polymer-blend system that is used in the analysis container. Generally, the frequency range of 4000 to 10,000 cm$^{-1}$ (2500 to 1000 nm wavelength range) is more than adequate to obtain useable NIR property calibrations for all structural polymers suitable for containers. The specific wavelength regions that are needed for NIR analysis of all major polymers are well known in the art.

The requirement of successful operation in $CO_2$ headspace quantification is simpler. The primary requirement is that the container sidewall material must not absorb too strongly around the 5000 cm$^{-1}$ (2000 nm) region where the $CO_2$ overtone band, i.e., the band that is most useful for analysis, is located. Fortunately, this requirement is met for all commercial packaging polymers, and therefore, will generally be met for NIR absorbances of blends, composites and laminates.

Figure 2:
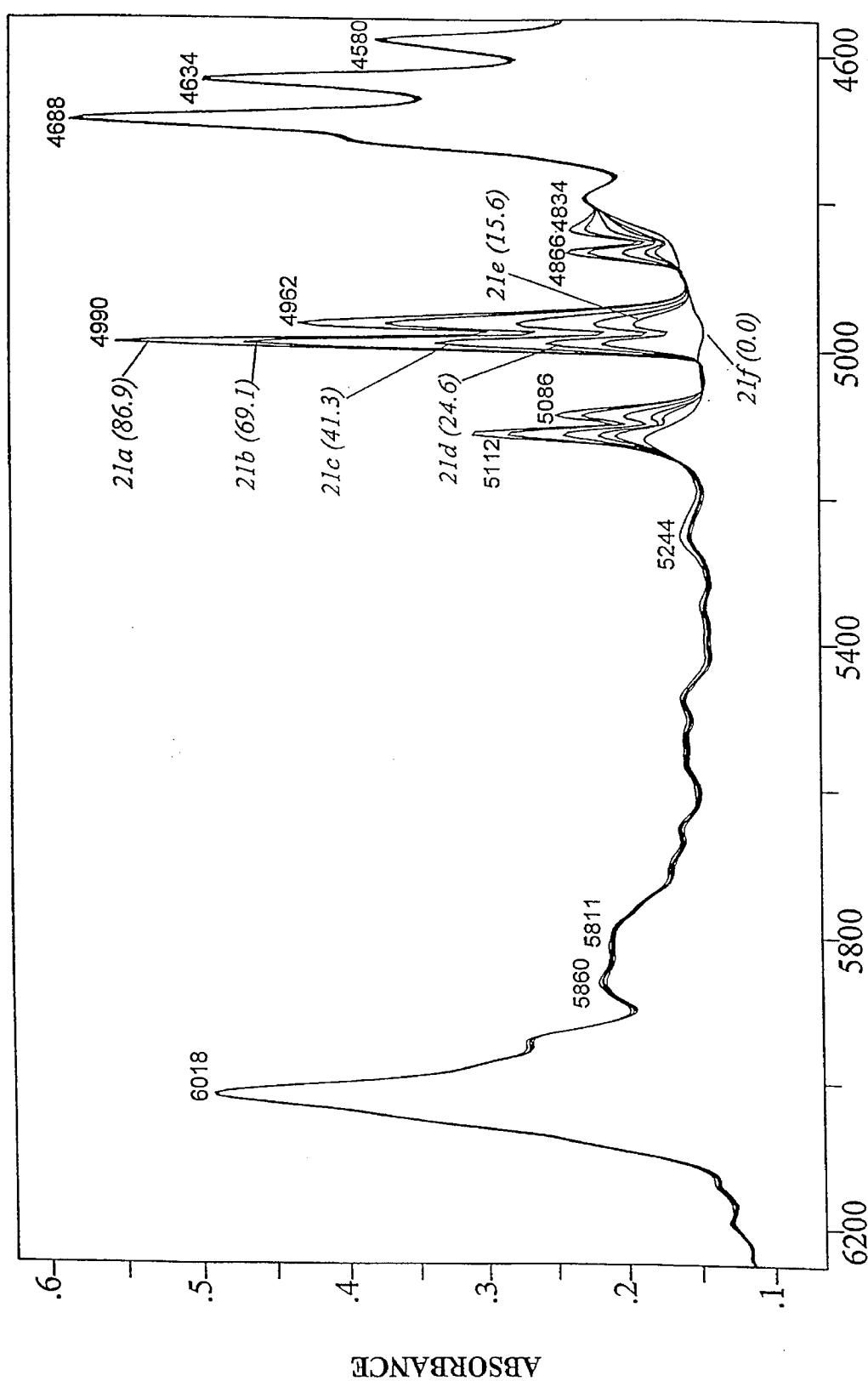
FIG. 2 is a near infrared spectral response chart for a analysis container.
Figure 3:
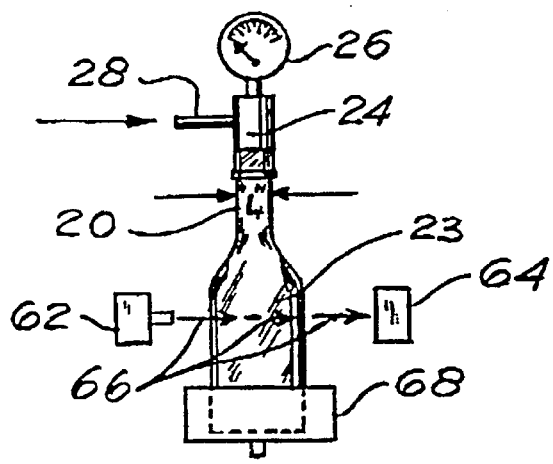
FIG. 3 is an elevation view of a analysis container illustrated mounted in a spectroscopic test apparatus which is shown schematically.

The chart of FIG. 2 illustrates the near infrared spectral response obtained for an analysis container and illustrates the spectral variation with $CO_2$ pressure. FIG. 2 is an overlay of the near infrared spectral response for a plurality of different values of $CO_2$ pressure ranging from 0 to 86.9 psia, the response patterns being indicated by reference numerals 21a–21f in FIG. 2. The pressure values, such as 86.9, 69.1, etc., (psia) are marked on the patterns. The analysis container 20, shown in FIG. 3, is a 500 milliliter PET bottle having a headspace pathlength "L" of 67 mm. The thickness of the sidewall in the headspace region of the container is approximately 28.2 mils. The analysis container is selected from a batch of containers made of plastics material, such as PET, and which are produced in a conventional manner, such as by blow molding.

I have identified those absorption bands in the NIR region that are important for quantitation of $CO_2$ concentration (or pressure). There are actually six bands between about 4840 and 5120 cm$^{-1}$ which vary in intensity simultaneously with $CO_2$ pressure. The main $CO_2$ band around 5000 cm$^{-1}$ is actually three doublets at 5112, 5086, 4990, 4962, 4866 and 4834 cm$^{-1}$. It is believed that this band is a stretching overtone and that this band is well separated from other spectral features. The peak response (height or area) is linear over a range of 0 to 90 psia $CO_2$ for the analysis container and there is negligible wavelength shift with variation in $CO_2$ pressure. The peak response for the analysis container follows Beer's law almost exactly. The molar absorptivity of this band is slightly perturbed by the presence of water vapor, but the peak frequencies are invariant, i.e., they demonstrate better than 1 cm$^{-1}$ stability, with $CO_2$ pressure or headspace humidity level. There are also minor $CO_2$ overtone or combination bands (not shown) observable at 4050 and 6982 cm$^{-1}$. It is likely that one of these bands corresponds to $CO_2$ dissolved in the plastic and thus solubility can be separately determined from the diffusion rate.

All of the other lines in the NIR for the spectrum illustrated in FIG. 2 are essentially invariant with $CO_2$ pressure, but do vary with PET thickness and properties. The main PET features are the combination bands 4000 to 4700 cm$^{-1}$ (partially shown in FIG. 2), the first overtone bands 5500 to 6200 cm$^{-1}$, and the second overtone bands 6900 and 7400 cm$^{-1}$ (not shown in FIG. 2). These bands generally follow Beer's law closely for sidewall thickness and are invariant in frequency with thickness.

I have determined that a few of the NIR PET bands vary appreciably with density/crystallinity when thickness is normalized. The general trends are a sharpening of bands (lesser peak width) as crystallinity increases, a small frequency shift of the 4688 and 6018 bands, and a variation of intensity for peaks at 4174, 4280, 4426, 4800, 5115, 5811 cm$^{-1}$ and a few others. The spectral variations with crystallinity in the region between 3900 and 5900 cm$^{-1}$ can be used for crystallinity estimation. Also indicated in FIG. 2 is the variation of the band at 5244 cm$^{-1}$. This feature is primarily sensitive to moisture content in the bulk PET material.

The measurement of the physical properties in the calibration step 10 is an actual direct measurement of particular characteristics of the analysis container 20 (FIG. 3), e.g. an observable, measurable quantity such as, for example, one or more of the following:

(a) the density of the resin forming the sidewall of the analysis container;

(b) the sidewall thickness of the container in the headspace region 22 of the container;

(c) the sidewall thickness of the container in the middle portion 23 of the container;

(d) the pathlength "L" of the headspace of the container; and, (e) the diameter "D" of the container in the middle portion 23 of the container.

The foregoing list is only illustrative of the types of physical properties for which the invention can be applied, and is not an exclusive list thereof. Although the invention is applicable to many different physical properties, the invention is particularly applicable to those characteristics or physical properties, such as density and crystallinity, of a container which are most difficult to measure directly. Moreover, a direct measurement of rate of carbonation loss, which is indicative of carbon dioxide retention level and thus product shelf-life, can take up to several weeks.

Using the principles of this invention, once a prediction model 12 has been established by the calibration step 10, no further direct measurements of gas pressures or physical properties of production containers are required. The production step 11 utilizes spectroscopic measurements which can be obtained quickly (e.g. in a few minutes or less) in conjunction with the prediction model 12 to provide an indication of physical properties of a test container and to estimate what the carbonation retention level will be depending upon gas pressure level and other physical properties being modeled, without actual direct measurement thereof. An accurate value for the carbonation retention level and other physical properties, can thereby be obtained in minutes, or less, instead of several weeks.

For headspace monitoring, the method according to the invention works best with an approximately cylindrical container. The predominant style for carbonated beverage containers is cylindrical because such containers are pressure vessels. The maximum height of the analysis container that can be accommodated is dictated only by fixturing to position the analysis container in place with the headspace located in the path of the NIR beam. The maximum diameter amenable to placement directly in the NIR beam, for a conventional center-focus spectrometer, is about five inches or 125 mm. However, normally, the headspace diameter present in the beam will be considerably less, such as on the order of 25 to 40 mm. This diameter is less than the typical gas-cell pathlength, 100 mm, that is used in single-pass NIR or mid-IR optical configurations. Thus, no divergence problems are created.

The method according to the invention can also be used for headspace monitoring of non-cylindrical containers. Despite the asymmetry of such containers, the finish is always cylindrical, thus limiting asymmetry in the neck region. The headspace concentrations and the headspace path are both calibrated and rotational averaging can be performed for calibrations of a given container style, thus including any asymmetry in the calibration data.

There are other polymer and container properties that can be accessed by straightforward application of the teachings of this invention, i.e., calibration for moisture content or for intrinsic viscosity. Also, an orientation function that is related to average polymer chain extension for a chosen location on the container sidewall can be obtained by adding an NIR polarizer and measuring the transmission at orthogonal polarizations.

Figure 5:
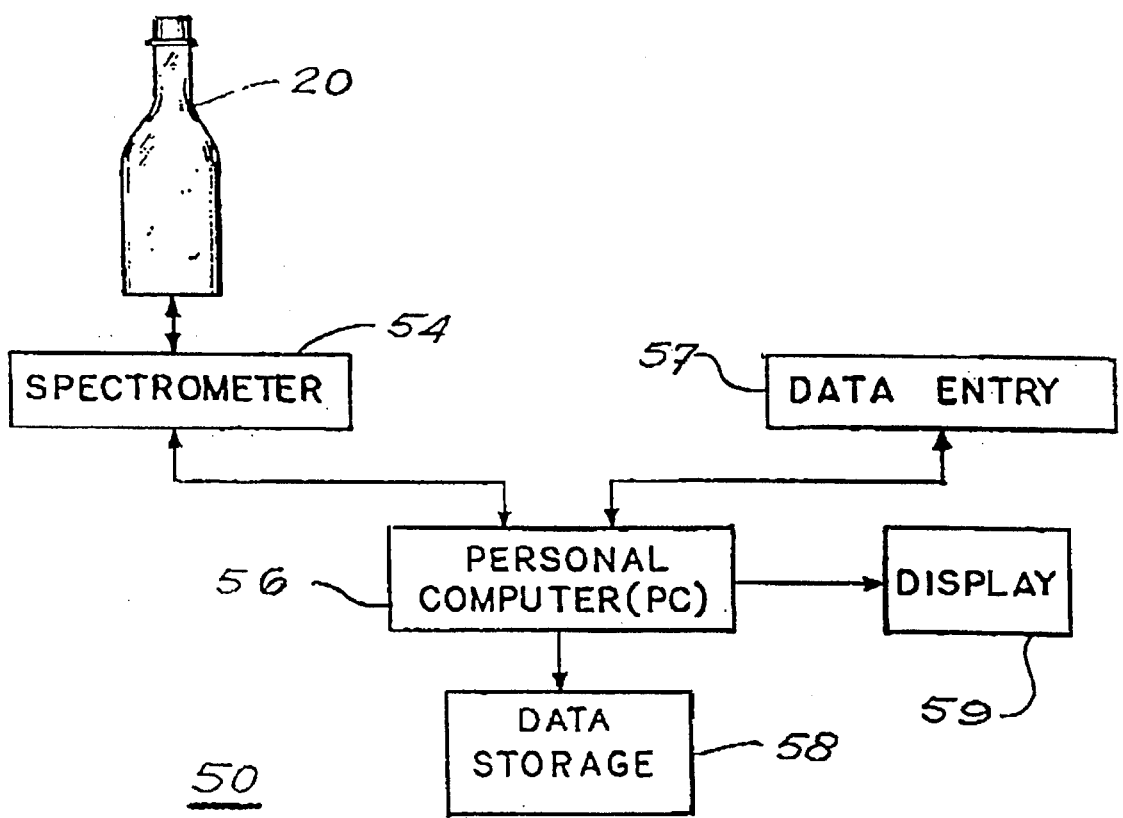
FIG. 5 is a block diagram of apparatus for carrying out the method of the invention.

Referring to FIG. 5, there is illustrated a block diagram of apparatus 50 for carrying out the method of the invention. The apparatus 50 includes a spectrometer 54 which is controlled by a computer 56 which has an associated data storage device or a data memory 58. A data entry means 57 permits data to be entered into the computer 56 for processing thereby and storage in the data storage device 58. The computer 56 can be a personal computer such as that known to those skilled in the art as an IBM compatible personal computer. The computer can include the data memory 58 which comprises suitable facilities for storing the composite spectrum ultimately produced as a file on a disk drive on the personal computer, referred to herein as a composite spectrum file. The composite spectrum file containing the spectral data is thereby available to other software executing on the personal computer for further processing as described below. The computer 56 has an associated data display device 59, which can be a CRT display as is conventional and/or a conventional printer for providing a visual display, and/or printout, of information including calibration data stored by the computer or information resulting from processing of the data by the computer.

Any standard center focus Fourier Transform IR (FTIR) spectrometer is suitable for this application. The spectrometer in this embodiment is operated in transmission mode, with the headspace (or body) of the analysis container positioned midway between the IR source and the IR detector. For the analysis container 20 illustrated in FIG. 3, the source 62 and the detector 64 are positioned on axis with the body 23 of the container. For a test container 20a illustrated in FIG. 8, the source 62 and the detector 64 are positioned on axis with the headspace 24 of the container. A raw sample spectrum for analysis container is then obtained. The sample spectrum can be corrected for baseline offset as is known in the art. The spectrometer operates under the control of the computer 56. Accessories provided with commercially available spectrometers include a parallel data interface to the personal computer and software executable on the personal computer for carrying out the above described spectroscopy.

Referring again to FIG. 4, the calibration step 10 is now described in more detail. The preparation of the prediction model 12 is illustrated with regard to an analysis container which is selected from a batch of containers made of plastics material, such as PET, and which are produced in a conventional manner, such as by blow molding. This is represented at block 30 in FIG. 4, where a container to be analyzed is selected from a batch of containers that are produced in a conventional manner. Obviously, the method of the invention also can be used in analyzing prototype containers in developing parameters both for a production process and for containers to be produced. At block 31, the selected analysis container 20 (FIG. 3) is subjected to actual physical measurements. For the exemplary embodiment, the physical properties measured include the diameter "D", the thickness of the sidewall of the container, the headspace pathlength "L" and the wall thickness in the headspace region 22 of the container, and the measurement data is obtained by actual physical measurement of the container 20 is performed. The measurement data thus obtained is added to the calibration set as indicated at block 32.

Figure 6:
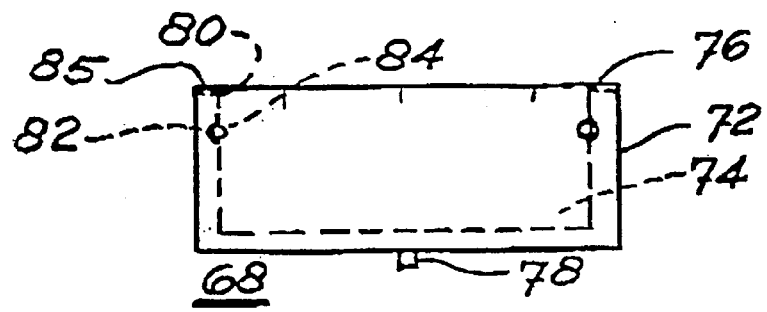
FIG. 6 is a top plan view of a test fixture for holding a container in a spectrometer during analysis of the container.
Figure 7:
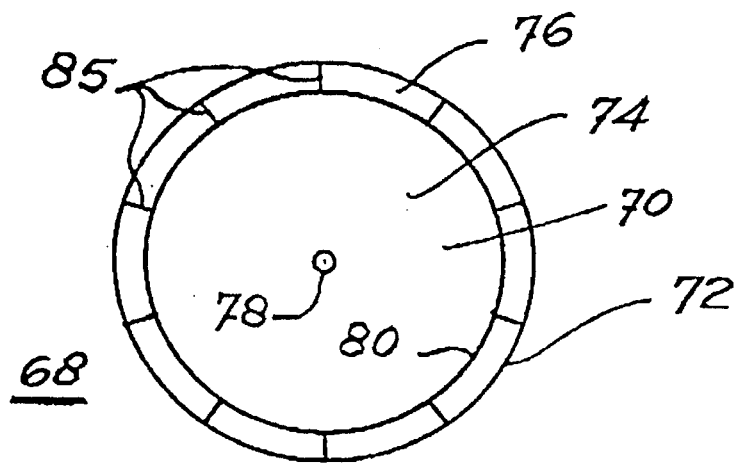
FIG. 7 is a side view of the test fixture shown in FIG. 6.

Referring to FIGS. 3, 6 and 7, to perform the spectroscopic analysis, the container 20 is placed in a test fixture 68 that is adapted for holding the container during the NIR spectroscopy. In particular, the test fixture 68 can form a part of the commercially available FTIR spectrometer, but is preferably a custom adapter jig, such as test fixture 68 illustrated in FIGS. 3, 6 and 7. The test fixture is a generally cup shaped member made of aluminum or other suitable material. The test fixture has a generally flat bottom 70 and a sidewall 72. The outer diameter of the test fixture is 88 mm and the inner diameter is 80 mm. The height of the side wall 72 is 42 mm from the upper surface 74 of the bottom to the upper edge 76. The test fixture has a centering pin 78 projecting downwardly from its bottom surface for mounting on the spectrometer. In one embodiment of the test fixture, the pin 78 has a 3.9 mm outer diameter for providing a snug fit in a 4 mm hole of the spectrometer. The inner surface 80 of the sidewall has an annular groove 82 therein near its upper edge which receives an O-ring 84 for providing snug mounting of the container within the fixture to maintain the container in position in the holder. The test fixture 68 positions the analysis container within the spectrometer with its headspace centered in the beam of the instrument for permitting transmission of IR radiation directly through the container headspace from source 62 to detector 64, as indicated by arrows 66. The test fixture is rotatable within the spectrometer to permit the analysis container 20 to be controllably rotated between various positions, if desired, for multiple view scanning arrangements. The upper surface of the sidewall is scribed at 36 degree segments for defining ten index marks 85 for facilitating multiple view IR scanning of the container.

The test fixture 68 is particularly suitable for supporting the container in the spectrometer when the container is filled and capped. The container is filled with a suitable gas which, in the exemplary embodiment is carbon dioxide, for pressurizing the analysis container 20, block 33. The pressure within the container is monitored in a suitable manner such as by the use of a pressure gauge 26 which is mounted in the neck of the container by way of an adapter 27 that includes an inlet 28 that is adapted for connection to a source of the carbon dioxide gas. If the container is empty, as when only physical characteristics of the container are being monitored, the finish portion of the container can be threaded into a mating holder for supporting the container within the spectrometer.

Referring again to FIG. 4, at block 34, the analysis container is subjected to spectroscopic analysis. The spectroscopic analysis is preferably performed in the near infrared ("NIR") spectrum, although the invention in general is not limited thereto. The IR measurements are carried out at different pressures with the pressure within the container being varied by adjusting the pressure of the carbon dioxide supplied to the interior of the container. In the exemplary embodiment, the analysis container is not liquid filled and the IR transmission path is through the middle portion of the container as illustrated in FIG. 3. The near infrared transmission through the container is measured, thereby capturing information about the container walls and the gas concentration in the container. Although not illustrated in the drawings, the analysis container 20 can be filled with a liquid and then pressurized, in which case, the IR transmission path is through the headspace and the measurement data is the gas concentrations or gas pressure in the headspace when the container is filled with liquid under pressure and then capped, as for the test container 20a shown in FIG. 8. In either case, the IR analysis requires about six to twenty-four seconds for a single view and about one to two minutes for multiple views as the analysis container is being rotated from view to view.

The computer 56 (FIG. 5) provides a display and/or a print out of qualitative or quantitative information. If the container is empty, the reports include properties of selected materials, information as to uniformity and dimensions of the analysis container. The report also shows model residuals, i.e., deviation of the test sample spectrum for each of the calibration models. If the container is pressurized or filled, the report additionally includes the headspace $CO_2$ concentration and/or related shelf-life parameters.

Collectively, all of the spectra and quantitative measurements of the physical properties corresponding thereto, are stored together in a data structure referred herein to as a calibration set. The calibration set is maintained as a data file on a disk drive, or other suitable storage media, within a computer which will process the calibration set as described in greater detail below. Preferably, the same personal computer as used for the spectroscopy described above can be used for this purpose, although the transfer of the various files between computer systems and the sharing of files over networks are also well known in the art and can be utilized with this invention. The calibration set can be structured as a list containing two associated entries for each sample run, those entries being (1) the numerical value corresponding to the physical property measurement for the sample obtained in block 32, and (2) a file name, specifying the composite spectrum file which contains the corresponding spectrum for the same sample. As previously noted, the composite spectrum file is stored directly on the personal computer as a part of the spectroscopy operation. The numerical value corresponding to the physical property is typically a single number, and can therefore be easily entered manually into the calibration set.

Thus, after completing physical and NIR spectral measurements of the analysis container and recording the respective results at blocks 32 and 35, a decision is made at block 36 as to whether sufficient data has been collected for the current calibration step 10. The calibration step 10 has somewhat of a statistical nature, in that the quality, or accuracy, of the prediction model finally produced depends on (a) the number of samples included in the calibration set, and (b) the range of process conditions used in obtaining the samples in the calibration set. The first criteria (a) should be self-evident to those skilled in the art. If a greater number of samples are included in the calibration set, then the values obtained will tend to be distributed about statistical norms, and therefore be more insensitive to individual aberrations. The second criteria (b) is important in ensuring that the prediction model 12 developed is valid over a range of process conditions. Specifically, the prediction model 12 should preferably be valid over that range of process conditions for which the prediction model 12 is expected to be used. In other words, while it would be possible to construct a calibration set which includes samples taken using only one process condition, the resulting prediction model 12 could be expected to yield accurate results only for that single process condition, or process conditions nearly the same. According to the invention, however, it has been discovered that by including samples in the calibration set which are obtained over a range of process conditions, a prediction model 12 can be achieved which is usable and valid over an entire range of process condition. For example, the prediction model 12 can be used in a production environment which is expected to produce containers having a material distribution, such as side wall thickness, which ranges from approximately 28 mils to 31 mils. In that case, the calibration set will preferably include samples prepared with various thicknesses distributed throughout that range. Process conditions other than thickness can also be varied over specific ranges, including temperature, pressure, and chemical constituents used in the resin.

A more detailed discussion of the range of values for which the prediction model 12 is valid is presented below in relation to the actual computations used for producing the prediction model 12. For now, it is sufficient to note that the samples included in the calibration set are sufficient in number and cover a predetermined range of process conditions.

As a general guideline, applicant has found that a calibration set which includes sixteen analysis containers and five views has been found to yield a prediction model with satisfactory accuracy over the same range of process conditions. Therefore, the choice of the number of analysis and the process conditions under which the analysis are obtained, may vary, and is decided based on the prediction model 12 desired. The test at block 36 of FIG. 4 therefore, is a decision as to whether the samples for the calibration step 10 have been completed. If more samples are needed, then a branch is taken back to block 30, where additional samples are taken, possibly under different process conditions as discussed above. A loop is thereby established to obtain samples until the calibration set is complete.

The foregoing process is performed for each of the analysis containers. A composite spectrum is then constructed by coherently averaging the final sample spectra from all five views. The composite spectrum is thus a single spectrum which corresponds to the analysis container 20 in the aggregate. Once the calibration set is found to contain all of the desired analysis at block 36, a branch is taken on to block 37.

Figure 4:
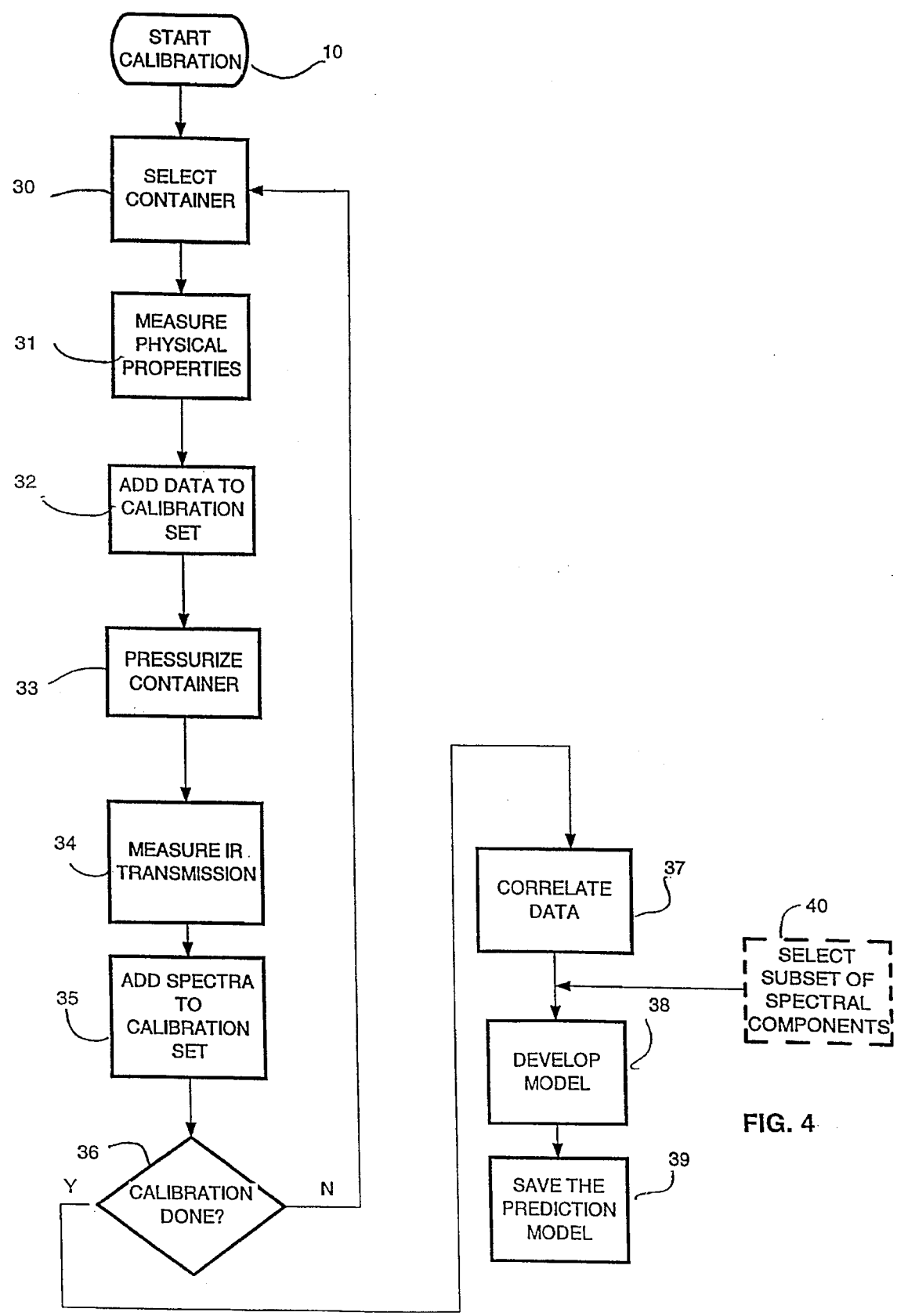
FIG. 4 is a process flow chart for the calibration step of the method depicted in FIG. 1.

Still referring to FIG. 4, correlation computations are performed in block 37 to produce the correlation coefficients for each spectral component with respect to the physical property of interest.

The specific correlation computations performed in block 37 can be performed, for example, using generalized commercially available software. One software that is particularly suitable for this application in which carbonation retention loss prediction is a factor, is sold commercially as a software package PLSPlus marketed by Galatic Industries Corporation, Salem, N.H. The PLSPlus software is usable in an environment utilizing LabCalc software available from Galactic Industries Corporation, Salem, N.H. The LabCalc environment executes directly under a Disk Operating System (DOS) on an IBM compatible personal computer. Another suitable software, available from Galatic Industries, is GRAMS/386 which executes under the "windows" environment, the latter being a graphical environment separately available from Microsoft, Inc., and also executable on an IBM compatible computer using an Intel 80386 microprocessor. The GRAMS/386 environment has been found by applicant to provide substantially faster execution times, and is therefore generally preferred. In this embodiment, the software is preferably executed on the same personal computer that is used in performing the spectroscopy described above. Other commercial software products that can perform equivalent computations include the Unscrambler, marketed by Camo AS, Trondheim, Norway, and ISI, marketed by Infrasoft International, Port Matilda, Pa.

Commercially available software includes conventional routines to compute raw correlations between each spectral component in a given calibration set and the physical property or concentration (or pressure) of interest. The raw correlations for individual spectral components can be positive or negative, and may be strong or weak. Assuming that the correlation coefficients are standardized between +1 (strongest positive correlation) and −1 (strongest negative correlation), then the correlations are considered "strong"

when the coefficients are near +1 or −1. Conversely, coefficients near zero indicate weak correlations. If a particular correlation includes at least some strongly correlated spectral components, then the accuracy of the prediction model 12 should be quite good. If on the other hand, none of the spectral components correlate strongly to the concentration of interest, then the accuracy of the prediction model 12 for the particular concentration or property under investigation will be poor and may or may not be usable, depending upon the accuracy desired.

The subsequent processing steps of the calibration procedure illustrated in FIG. 4, assume that at least some spectral components strongly correlate to the physical property of interest. In that case, a prediction model 12 can be computed as shown in block 38. However, before proceeding to block 38, an optional step shown by dotted lines 40 may be performed in order to improve the accuracy of the prediction model 12 eventually produced. Specifically, the optional step 40 can be used to select a subset of the spectral components for further processing, in which the selected subset contains only those spectral components that are the most strongly correlated to the particular physical property of interest. For example, a spectral subset can include only those components, or "bands" of adjacent spectral components, which have correlation coefficients with an absolute value greater than a predetermined threshold value. The optional step 40 is not essential to the invention, because a prediction model 12 can be produced based simply on the entire spectrum. However, the step 40 is generally preferred because it results in a more accurate model, particularly in those cases where a relatively fewer number of spectral components are strongly correlated. The PLSPlus software includes a facility for specifying specific spectral components or bands to be used in subsequent computations, which can be used to perform the operation indicated in block 40, if desired.

In block 38, the desired spectral components (whole spectrum or selected subset) are further processed using a multivariate regression analysis to produce a prediction model. As generally known to those skilled in the art, multivariate regression analysis can be performed by the known techniques of K-matrix, partial least squares, principal components regression, and others. In this embodiment, the aforementioned software also provides a capability to perform the multivariate regression analysis. Specifically, the PLSPlus software includes a routine referred to as a "PLS" algorithm which performs a multivariate regression analysis. The calculation first computes a number of different prospective modeling functions with an increasing order of complexity, or "factor" number, as generally known to those skilled in the art. Each prospective modeling function is a function of "n" variables, where "n" is the number of spectral components selected for inclusion in the calculation. By default, prospective modeling functions are computed for a number of factors equal to half of the number of samples in the calibration set. For example, if the calibration set includes four samples, then two prospective modeling functions are computed by default, corresponding to factors one and two, respectively. The default choice for the number of prospective modeling functions can of course be overridden, if desired, to specify a greater or lesser number of prospective modeling functions to be computed. Once the prospective modeling functions have been calculated, the routine performs a cross-validation in the known manner to compute the expected prediction error corresponding to each prospective modeling function using a one-sample-out cross-validation rotation. The estimated error typically drops rapidly with an increasing number of factors until a minimum is reached. The prospective modeling function which exhibits the minimum estimated prediction error is then preferably chosen to be the prediction model 12.

Finally, at block 39 the prediction model 12 is saved on disk, or other suitable storage media. The prediction model 12 as produced by the PLSPlus software used in this embodiment is a formatted file, encoded with information including (a) the order, or "factor" number of the modeling function, (b) the number of spectral components used, "n", and the specific spectral components, or bands, which participate in the modeling equation, and (c) the coefficients for the modeling equation.

Figure 8:
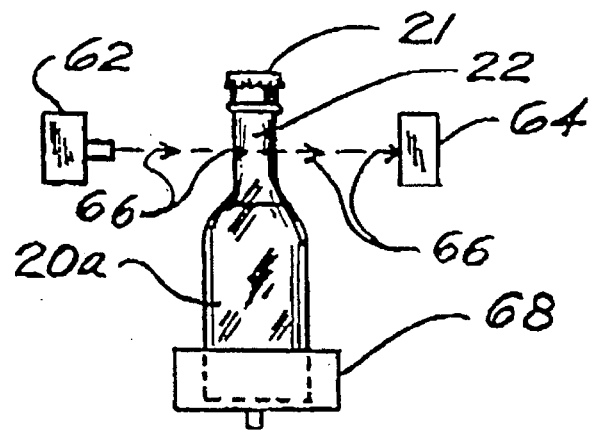
FIG. 8 is a view similar to that of FIG. 3 and showing a container that is filled with a liquid under pressure and capped.

Referring again to FIG. 1, the prediction model 12 developed by the calibration step 10 described above is utilized to estimate one or more physical properties of a selected container in the production step 11. Typically, this aspect of the invention can be used, for example, to obtain an estimation of carbonation retention level and/or to verify that a (or several) selected container property has the desired physical characteristics as a part of a quality control program or for product statistics. The production step 11 begins at block 13, where a number of production containers are produced under substantially the same process conditions. One of the containers is selected to be the test container 20a (FIG. 8). By way of example, it may be desired to select one test container 20a in each batch of production containers, or one test container 20a for each 100 or 1,000 production containers (not necessarily in the same batch), and so on. These would of course be the same quality control or statistical procedures as used in the prior art, except that according to the invention, the test container 20a is analyzed by spectroscopic analysis rather than direct measurement of the physical property of interest. The production containers, including the test container 20a, are then filled in the usual manner.

Referring additionally to FIG. 8, the test container 20a is subjected to spectroscopic analysis as indicated in block 15, again in a manner similar to that used in the calibration step 10 as described above. However, in the production step 11 the resulting spectrum obtained in block 15 is used as input data for the prediction model 12. It will be understood by those skilled in the art that evaluation of the prediction model 12 is carried out by a suitable computer with appropriate software. For example, the aforementioned commercially available software, running on an IBM compatible personal computer, includes routines suitable for evaluating the prediction model 12 based on the measured spectrum 15.

The result of evaluating the prediction model 12 for the particular spectrum from block 15 results in an estimated value for the carbonation level and/or the physical properties of interest, as represented by block 16. Again considering the example of determining carbonation level which is a measure of carbonation retention, the numerical result at block 16 is, in effect, an accurate indication of these properties. In fact, the computation of carbonation retention is a principal application of the invention, since it results in an amazing reduction in both the time and the complexity of the apparatus required when compared to prior methods for direct measurement of the carbonation level (minutes versus weeks, respectively).

Finally, the estimated carbonation level and the estimated physical property from block 16 are output at block 17, e.g. utilized for an appropriate purpose such as the aforementioned quality control or product statistics. Even though the estimated values are not necessarily as exact as that which could be obtained by direct measurement, it has nevertheless been found by applicant to be a highly accurate estimation thereof. With suitable care with respect to preparation and verification of the prediction model 12 as described herein, an estimation with a Standard Error of Prediction (SEP) of less than 10% relative should be easily attainable. For applications, such as quality control and product statistics, where a general indication rather than absolute accuracy is desired, this invention provides a drastic improvement in both speed and simplicity.

As an optional step (not shown), it may be desirous to separately verify the prediction model 12 based upon containers from the finished product batch. In the calibration step 10, the results can be subject to self-prediction, e.g. the result has been optimized with respect to the samples only in the calibration set. The true accuracy of the prediction model 12 can be verified independently by performing actual, direct measurement of the physical properties of interest for some of the finished product containers, and comparing the value thus obtained to the value estimated by the prediction model 12. In tests of this type performed by applicant, the prediction model 12 has been found to have an accuracy acceptable for production purposes, i.e. for quality control or product statistics. However, if a particular verification of this type should result in an unacceptable accuracy, then it would be necessary to repeat the calibration step 10, as necessary, until a suitable prediction model 12 is obtained. For example, the calibration step 10 could be performed with a different set of process conditions, perhaps with a more narrow range of process conditions, or with more samples, and so on. Of course, once the prediction model 12 has been verified in this way, further direct measurements would again be unnecessary.

In the exemplary embodiment, monitoring of containers is carried out by selecting a test container from a batch of production containers and removing the test container from the production line, before or after filling, and then subjecting the selected container to spectroscopic analysis. However, with modifications that will be apparent to those skilled in the art, the testing of selected production containers can be carried out on an automated basis whereby a suitable conveyance such as, for example, a moving belt (not shown) is utilized to automatically deliver the test containers to a test station for spectroscopic analysis. Alternatively, many other known conveyances can be utilized, including either manual or robotic positioning to accurately register the selected test containers with respect to the spectrometer source and detector for testing, including mechanical stops and position sensors (not shown).

It will be understood by those in the art that the present invention may be modified in a number of aspects without departing from the spirit of the invention and that while the invention has been described with reference to preferred embodiments, various modifications can be made without departing from the spirit and scope of the invention as defined in the appended claims. Further, the invention is equally applicable to other semi-crystalline polymers PAN, PEN, PETG copolymer and transesterified PET/PEN blends. Moreover, the invention can be used for unfilled PVC, PC, PS, acrylic and numerous other commercial polymers that are reasonably clear. These materials may not be suitable for carbonated beverages or even for blow molding. Nevertheless, selected material properties can be calibrated.

Additionally, the invention can also be used with containers made of clear multilayer materials, such as PET/EVOH/ PET, PVDC/PET OR $SiO_x$/PET. The thin $SiO_x$ layers will be essentially transparent to NIR and so are not amenable to $CO_2$ loss rate prediction, but will not interfere with headspace composition measurement or PET property estimation. Containers of PP or multilayer PP/EVOH/PP can be monitored, although excessive optical scattering may limit accuracy of calibrations.

Thus, it has been shown that the present invention has provided a method and apparatus for the rapid estimation of one or more physical properties of production beverage containers, and/or the gas concentration within the headspace of such containers, and in particular plastic containers which contain a carbonated beverage. The method includes preparing a prediction model based on correlations between an infrared absorption spectrum obtained from an analysis container and corresponding measured values of gas concentrations and physical properties of the analysis container. By the method of the invention, selected physical properties of production containers and/or gas concentrations within the headspace of production containers do not need to be measured directly, but rather can be estimated based on the prediction model with a measured infrared absorption spectrum as an input to the prediction model, thereby providing non-invasive monitoring of production containers, filled and pressurized.

I claim:

1. A method for measuring the concentration of at least one gas in the headspace of a plastic container that has been filled with a product and then sealed under pressure, said method comprising the steps of:

(a) preparing a prediction model which accepts as an input at least one spectral component value corresponding to absorption of electromagnetic radiation in at least one frequency band of the radiation, and which outputs an estimated measurement for the concentration of said at least one gas in the headspace of said container based on said input, said preparing step including the step of performing multivariate regression analysis on the spectral component value to produce the prediction model as an equation which maps spectral components as inputs to an estimated value for the pressure of said at least one gas;

(b) performing spectroscopic analysis of said container to obtain at least one spectral component value corresponding to the absorption of electromagnetic radiation in said at least one frequency band by said at least one gas; and (c) evaluating the prediction model with said at least one spectral component value as the input, wherein the output of said prediction model is thereby a measurement of the concentration of said at least one gas in the headspace of said container.

2. The method of claim 1, wherein the step (b) of performing spectroscopic analysis of said container obtains a plurality of spectral component values which correspond to the absorption of electromagnetic radiation in a plurality of different frequency bands by said at least one gas.

3. The method of claim 1, wherein said electromagnetic radiation is in the infrared spectrum.

4. The method of claim 1 wherein said one gas is carbon dioxide.

5. A method for measuring the concentration of at least one gas in the headspace of a plastic container that has been filled with a product and then sealed under pressure, said method comprising the steps of:

(a) preparing a prediction model which accepts as an input at least one spectral component value corresponding to absorption of electromagnetic radiation in at least one frequency band of the radiation, and which outputs an estimated measurement for the concentration of said at least one gas in the headspace of said container based on said input;

(b) performing spectroscopic analysis of said container to obtain at least one spectral component value corresponding to the absorption of electromagnetic radiation in said at least one frequency band by said at least one gas;

(c) evaluating the prediction model with said at least one spectral component value as the input, wherein the output of said prediction model is thereby a measurement of the concentration of said at least one gas in the headspace of said container; and wherein step (a) for preparing the prediction model further comprises the steps of:

(d) measuring at least one physical property of an analysis container to thereby obtain first measurement data representing a measured value for said at least one physical property;

(e) filling said analysis container with said at least one gas under pressure;

(f) measuring the pressure within said analysis container to obtain second measurement data representing the pressure within said analysis container;

(g) performing spectroscopic analysis of said analysis container to obtain at least a first analysis spectral component value corresponding to said at least one physical property and at least a second analysis spectral component value corresponding to the absorption of electromagnetic radiation in said at least one frequency band by said at least one gas;

(h) computing correlations between at least said first analysis spectral component values and said first measurement data and between at least said second analysis spectral component values and said second measurement data; and (i) preforming multivariate regression analysis on the analysis spectral component values with respect to the measured value for pressure of at least said one gas and the measured value of said at least one physical property to produce the prediction model as an equation which maps spectral components as inputs to an estimated value for the pressure of said at least one gas and said at least one physical property as an output.

6. The method of claim 5, wherein (e) through (g) are performed utilizing a pressure condition in which the pressure is varied with each successive repetition of steps (e) through (g) within a predetermined range of pressures.

7. The method of claim 5, wherein the physical property is the thickness of the sidewall of said analysis container.

8. The method of claim 5 wherein said one gas is carbon dioxide.

9. The method of claim 5, wherein steps (d) through (g) are repeated for a plurality of different analysis containers to produce a calibration set including a plurality of sample sets, each sample set including said first measurement data, said second measurement data and said at least first and second spectral component values obtained by one of said plurality of repetitions of steps (d) through (g); step (h) is repeated to compute a plurality of correlation sets, each correlation set including the correlations for each said sample set in the calibration set; and step (i) is performed utilizing the entire calibration set and said plurality of correlation sets.

10. The method of claim 9, wherein the spectroscopic analysis of said plurality of analysis containers in step (g) produces a corresponding plurality of said second spectral component values; correlations are computed in step (h) for each of said plurality of spectral component values; a subset of spectral components is selected to include only those spectral components which are most highly correlated to the concentration of said at least one gas within each of said analysis containers and the selected physical property of said analysis containers according to the correlations computed in step (h); and the multivariate regression analysis in step (i) is performed on the basis of said selected subset of spectral components.

11. The method of claim 10, wherein the spectroscopic analysis in step (b) for said container filled with said product and in step (g) for said analysis containers are performed in a transmission mode.

12. An apparatus for measuring the concentration of at least one gas in the headspace of a container that has been filled with a product and then sealed under pressure, said apparatus comprising:

means for providing a prediction model which accepts as an input at least one spectral component value corresponding to absorption of electromagnetic radiation in at least one frequency band of the radiation, and which outputs an estimated measurement for the physical property based on said input;

means for performing spectroscopic analysis of said container to obtain at least one spectral component value corresponding to the absorption of electromagnetic radiation in said at least one frequency band by said at least one gas;

means for evaluating the prediction model with said at least one spectral component value as the input, wherein the output of prediction model is thereby a measurement of the concentration of said at least one gas in the headspace of said container; and said means for providing said prediction model including means for providing measurement data representing the pressure within an analysis container; means for performing spectroscopic analysis of an analysis container to obtain at least one spectral component value corresponding to the absorption of electromagnetic radiation in said at least one frequency band by said at least one gas; and processing means for computing correlations between said spectral component value and said measurement data and for performing multivariate regression analysis on the analysis spectral component values with respect to the measured value for the concentration of said at least one gas in said analysis container and to produce an equation which maps spectral components as inputs to an estimated value for the concentration of said one gas in said analysis container as an output.

\* \* \* \* \*